(12) United States Patent
Hines

(10) Patent No.: US 11,400,253 B1
(45) Date of Patent: Aug. 2, 2022

(54) PRESSURE-RELIEVING FINGER-MANIPULATED STRIP

(71) Applicant: Earle Hines, Dover, DE (US)

(72) Inventor: Earle Hines, Dover, DE (US)

( * ) Notice: Subject to any disclaimer, the term of this patent is extended or adjusted under 35 U.S.C. 154(b) by 48 days.

(21) Appl. No.: 17/164,878

(22) Filed: Feb. 2, 2021

(51) Int. Cl.
*A61M 21/02* (2006.01)
*A41B 15/00* (2006.01)
*A61M 21/00* (2006.01)

(52) U.S. Cl.
CPC ........... *A61M 21/02* (2013.01); *A41B 15/00* (2013.01); *A41B 2300/35* (2013.01); *A41B 2400/32* (2013.01); *A41B 2500/20* (2013.01); *A61M 2021/0022* (2013.01)

(58) Field of Classification Search
CPC .................................................. A61M 21/02
USPC ............................................... 40/661.04, 663
See application file for complete search history.

(56) References Cited

U.S. PATENT DOCUMENTS

| | | | |
|---|---|---|---|
| D130,965 S | 12/1941 | Fitch | |
| 5,416,928 A * | 5/1995 | Koenig | A41D 27/08 2/244 |
| 5,573,825 A * | 11/1996 | Brewster | G09F 7/02 428/483 |
| 5,871,214 A * | 2/1999 | Hummel | A63F 9/0208 273/348.4 |
| 10,426,299 B2 | 10/2019 | Snyder | |
| 10,589,058 B2 | 3/2020 | Smith | |
| 2003/0233717 A1 * | 12/2003 | Ortega | A47K 10/02 15/118 |
| 2004/0224121 A1 * | 11/2004 | Sheppard, Jr. | D03D 15/217 428/92 |
| 2005/0208848 A1 * | 9/2005 | Grossman | B63B 49/00 441/113 |
| 2005/0235533 A1 * | 10/2005 | Lemberger | G09F 23/00 40/360 |
| 2008/0178978 A1 * | 7/2008 | Power | A63B 41/125 150/154 |
| 2009/0149698 A1 | 6/2009 | Tastard | |
| 2013/0292537 A1 * | 11/2013 | Dirico | A47G 23/03 248/346.11 |

(Continued)

OTHER PUBLICATIONS

Yellow Owl Workshop ("Super Strong Brave Champion—Award Ribbon Card" available online at http://web.archive.org/web/20200809174408/https://yellowowlworkshop.com/products/super-strong-brave-champion-award-ribbon-card on Aug. 9, 2020) (Year: 2020).*

(Continued)

*Primary Examiner* — Kaylee R Wilson
(74) *Attorney, Agent, or Firm* — Kyle A. Fletcher, Esq.

(57) ABSTRACT

The pressure-relieving finger-manipulated strip is a mechanical structure. The pressure-relieving finger-manipulated strip is configured for use with a patient. The pressure-relieving finger-manipulated strip is a relaxation inducing device. The pressure-relieving finger-manipulated strip is rubbed by the patient to induce relaxation. The pressure-relieving finger-manipulated strip comprises a sheeting structure and a grommet. The grommet mounts on the sheeting structure. The pressure-relieving finger-manipulated strip forms the structure that generates that induced the relaxation response for the patient. The grommet forms an anchor point that allows the pressure-relieving finger-manipulated strip to clip to an externally provided structure.

12 Claims, 3 Drawing Sheets

(56) References Cited

U.S. PATENT DOCUMENTS

| | | |
|---|---|---|
| 2014/0215681 A1 | 8/2014 | Goodman |
| 2015/0202544 A1 | 7/2015 | Snee, Jr. |
| 2015/0273178 A1 | 10/2015 | Johnson |
| 2016/0098931 A1* | 4/2016 | Sears ...................... G09B 1/12 434/236 |
| 2017/0013922 A1* | 1/2017 | Vlad-Berindan ........ D04D 1/04 |
| 2018/0317674 A1* | 11/2018 | Richard ............... A47G 9/0223 |

OTHER PUBLICATIONS

Remove Before Flight (available online at http://web.archive.org/web/20201101035710/https://www.remove-before-flight.com/en/ on Nov. 1, 2020) (Year: 2020).*

* cited by examiner

PRESSURE-RELIEVING FINGER-MANIPULATED STRIP

CROSS REFERENCES TO RELATED APPLICATIONS

Not Applicable

STATEMENT REGARDING FEDERALLY SPONSORED RESEARCH

Not Applicable

REFERENCE TO APPENDIX

Not Applicable

BACKGROUND OF THE INVENTION

Field of the Invention

The present invention relates to the field of medical and veterinary including methods to induce sleep, more specifically, a mechanical structure for inducing relaxation. (A61M21/02)

SUMMARY OF INVENTION

The pressure-relieving finger-manipulated strip is a mechanical structure. The pressure-relieving finger-manipulated strip is configured for use with a patient. The pressure-relieving finger-manipulated strip is a relaxation inducing device. The pressure-relieving finger-manipulated strip is rubbed by the patient to induce relaxation. The pressure-relieving finger-manipulated strip comprises a sheeting structure and a grommet. The grommet mounts on the sheeting structure. The pressure-relieving finger-manipulated strip forms the structure that generates that induced the relaxation response for the patient. The grommet forms an anchor point that allows the pressure-relieving finger-manipulated strip to clip to an externally provided structure.

These together with additional objects, features and advantages of the pressure-relieving finger-manipulated strip will be readily apparent to those of ordinary skill in the art upon reading the following detailed description of the presently preferred, but nonetheless illustrative, embodiments when taken in conjunction with the accompanying drawings.

In this respect, before explaining the current embodiments of the pressure-relieving finger-manipulated strip in detail, it is to be understood that the pressure-relieving finger-manipulated strip is not limited in its applications to the details of construction and arrangements of the components set forth in the following description or illustration. Those skilled in the art will appreciate that the concept of this disclosure may be readily utilized as a basis for the design of other structures, methods, and systems for carrying out the several purposes of the pressure-relieving finger-manipulated strip.

It is therefore important that the claims be regarded as including such equivalent construction insofar as they do not depart from the spirit and scope of the pressure-relieving finger-manipulated strip. It is also to be understood that the phraseology and terminology employed herein are for purposes of description and should not be regarded as limiting.

BRIEF DESCRIPTION OF DRAWINGS

The accompanying drawings, which are included to provide a further understanding of the invention are incorporated in and constitute a part of this specification, illustrate an embodiment of the invention and together with the description serve to explain the principles of the invention. They are meant to be exemplary illustrations provided to enable persons skilled in the art to practice the disclosure and are not intended to limit the scope of the appended claims.

DETAILED DESCRIPTION OF THE EMBODIMENT

The following detailed description is merely exemplary in nature and is not intended to limit the described embodiments of the application and uses of the described embodiments. As used herein, the word "exemplary" or "illustrative" means "serving as an example, instance, or illustration." Any implementation described herein as "exemplary" or "illustrative" is not necessarily to be construed as preferred or advantageous over other implementations. All of the implementations described below are exemplary implementations provided to enable persons skilled in the art to practice the disclosure and are not intended to limit the scope of the appended claims. Furthermore, there is no intention to be bound by any expressed or implied theory presented in the preceding technical field, background, brief summary or the following detailed description.

Figure 1:
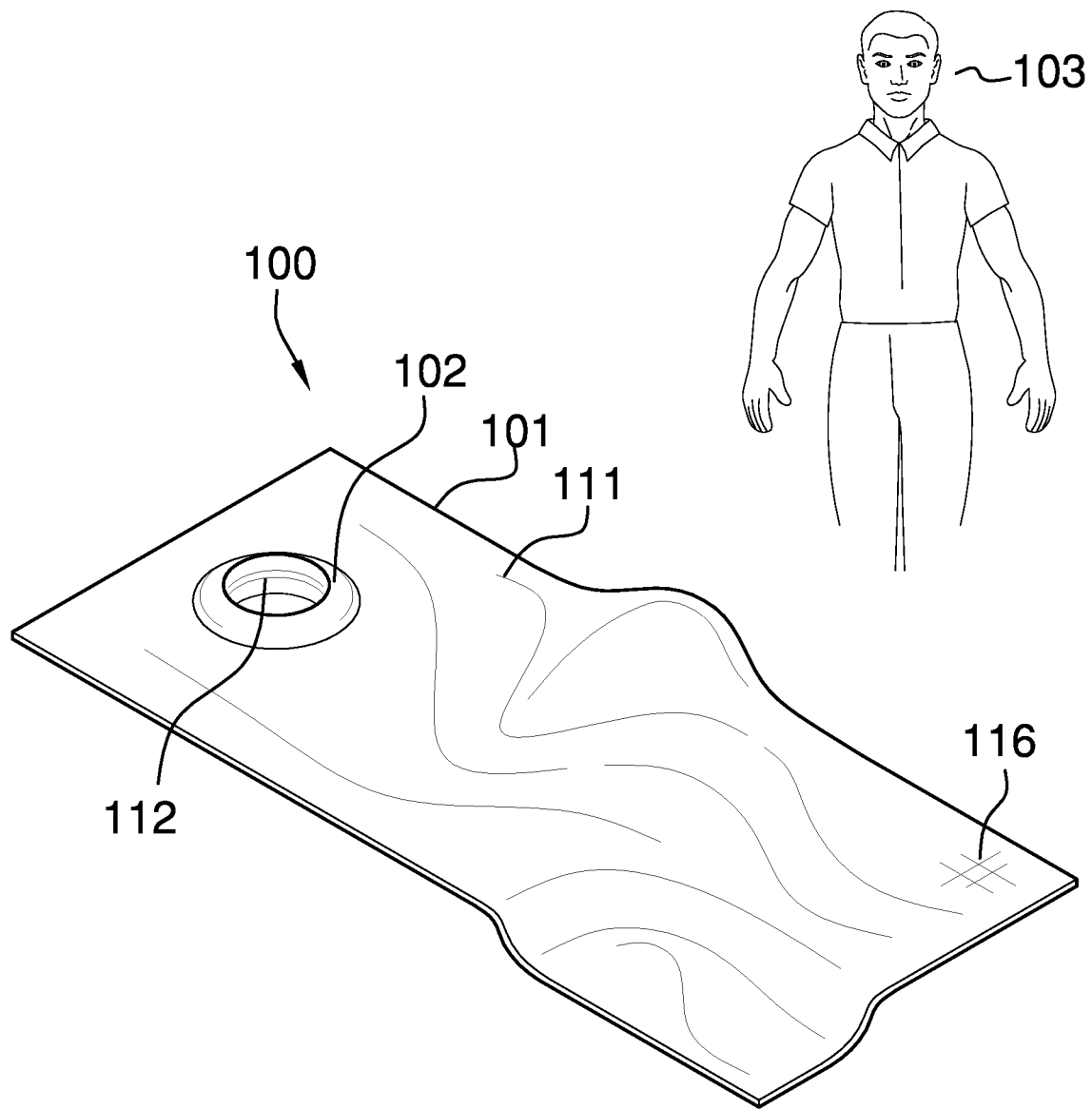
FIG. 1 is a perspective view of an embodiment of the disclosure.
Figure 2:
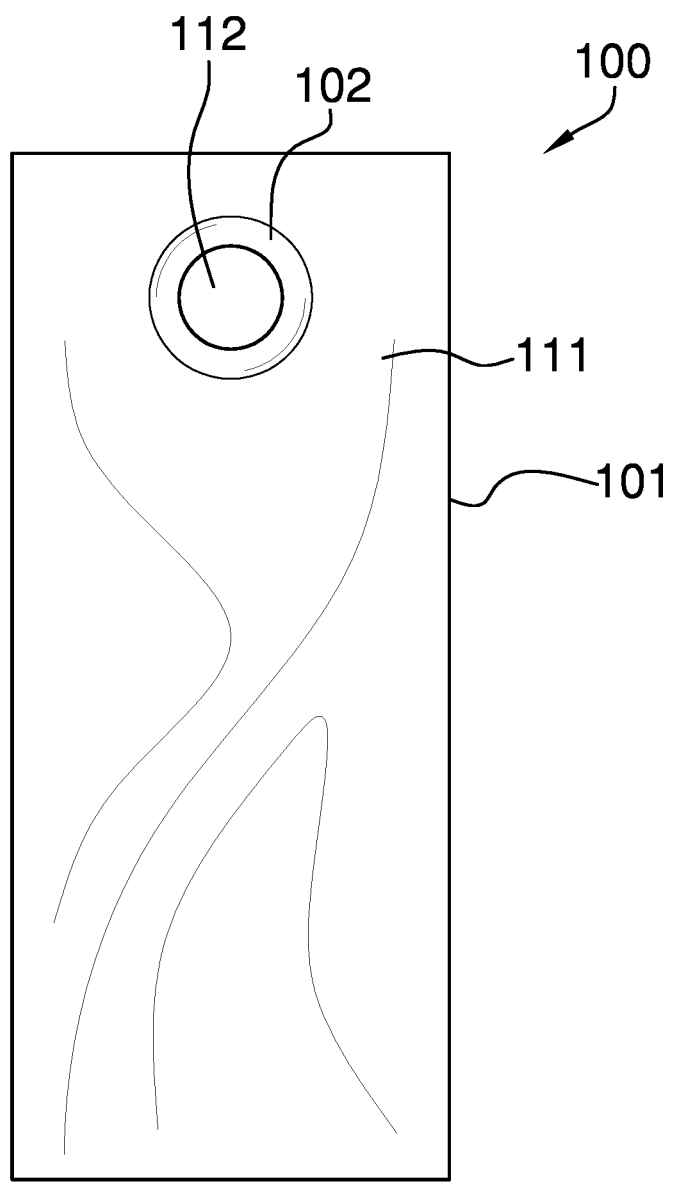
FIG. 2 is a front view of an embodiment of the disclosure.
Figure 3:
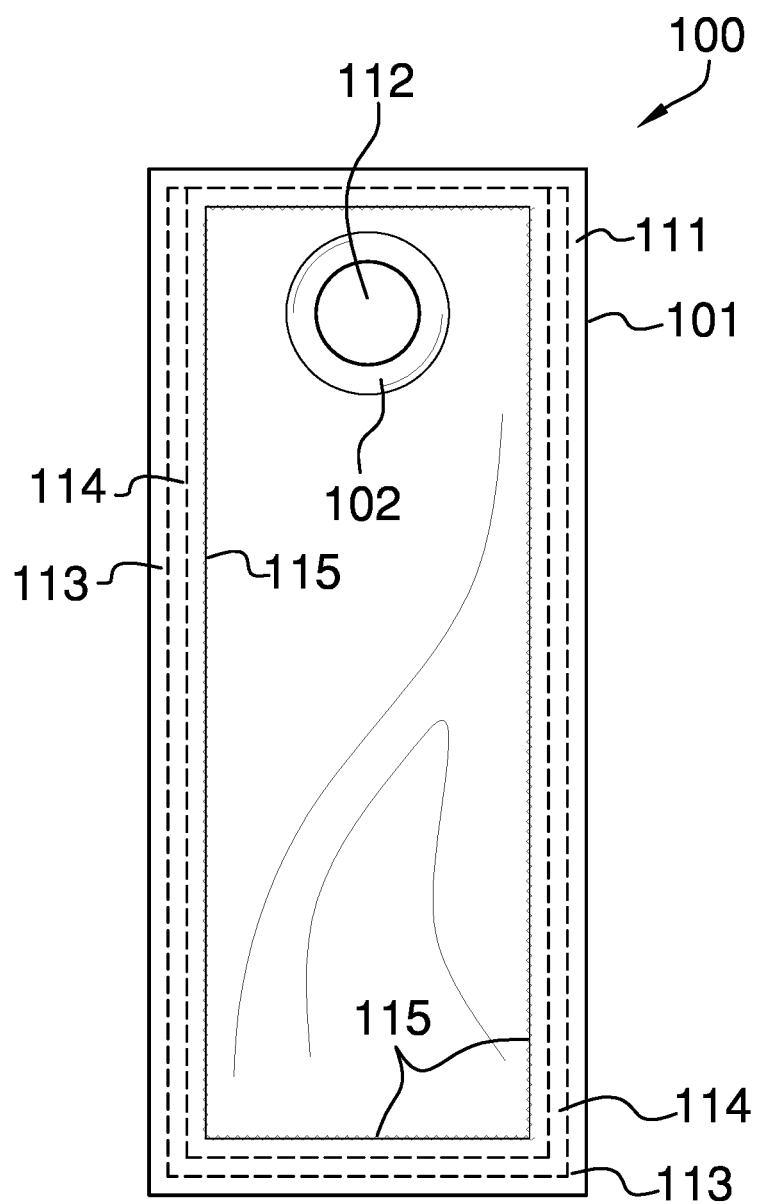
FIG. 3 is a front view of an alternate embodiment of the disclosure.

Detailed reference will now be made to one or more potential embodiments of the disclosure, which are illustrated in FIGS. 1 through 3.

The pressure-relieving finger-manipulated strip 100 (hereinafter invention) is a mechanical structure. The invention 100 is configured for use with a patient 103. The invention 100 is a relaxation inducing device. The invention 100 is rubbed by the patient 103 to induce relaxation. The invention 100 comprises a sheeting structure 101 and a grommet 102. The grommet 102 mounts on the sheeting structure 101. The invention 100 forms the structure that generates that induced the relaxation response for the patient 103. The grommet 102 forms an anchor point that allows the invention 100 to clip to an externally provided structure.

The patient 103 refers to an individual who uses the invention 100. The patient 103 is defined elsewhere in this disclosure.

The sheeting structure 101 is a flexible mechanical structure. The sheeting structure 101 is formed as a sheeting. The sheeting is defined elsewhere in this disclosure. The sheeting structure 101 forms the relaxation inducing structure. The patient 103 induces relaxation by manipulating the sheeting structure 101 with a hand. The sheeting structure 101 comprises a textile base 111 and a grommet 102 aperture 112.

The textile base 111 is a sheeting. The textile base 111 is a textile-based structure. The textile base 111 is formed from a plurality of yarns 116. The textile base 111 is formed using a satin weave pattern. Each of the plurality of yarns 116 used to form the textile base 111 comprises a silk yarn. The use of silk yarns provides for smooth surfaces on the textile base 111 that induces relaxation in the patient 103. The use of a satin weave for the textile base 111 produces a softness in the textile base 111 that induces relaxation in the patient 103.

The grommet 102 aperture 112 is an aperture that is formed the faces of the sheeting formed by the textile base 111. The perimeter of the grommet 102 aperture 112 is protected by the grommet 102. The grommet 102 aperture 112 forms an anchor point that allow the sheeting structure 101 to clip to an externally provided object for storage.

The grommet 102 is a mechanical structure. The grommet 102 is defined elsewhere in this disclosure. The grommet 102 attaches to the sheeting structure 101 such that the grommet 102 forms a protective structure around the perimeter of the grommet 102 aperture 112 of the textile base 111. The grommet 102 prevents damage to the grommet 102 aperture 112 from a fastening device, such as a clip, used to attach the invention 100 to an externally provided object, such as a backpack.

In a second potential embodiment of the disclosure, the textile base 111 further comprises a perimeter rouleau 113 and an elastic webbing 114.

The perimeter rouleau 113 is a rouleau. The rouleau is defined elsewhere in this disclosure. The perimeter rouleau 113 forms a structure on the face of the textile base 111 that encloses the elastic webbing 114. The perimeter rouleau 113 further comprises one or more seams 115.

Each of the one or more seams 115 is a sewn seam. The one or more seams 115 are used to form the perimeter rouleau 113. The one or more seams 115 secures the perimeter of the textile base 111 to the face of the textile base 111 to form the perimeter rouleau 113.

The elastic webbing 114 is a textile-based structure. The elastic webbing 114 is an elastic structure. The elastic webbing 114 is defined elsewhere in this disclosure. The elastic webbing 114 attaches to the face of the textile base 111 such that the elastic webbing 114 is enclosed by the perimeter rouleau 113. The elastic webbing 114 is attached to the face of the textile base 111 while the elastic webbing 114 is placed under tension such that the elastic webbing 114 draws the textile base 111 in on itself as the elastic webbing 114 returns to its relaxed shape. The elastic webbing 114 provides a resistive counterforce to deformations in the textile base 111 that further induces relaxation in the patient 103 during the use of the invention 100.

The elastic webbing 114 acts as a spring. Specifically, when a force is applied to both ends of the elastic webbing 114 in a direction parallel to the major axis of the elastic webbing 114, the applied force elongates the span of the end to end length the elastic webbing 114 in the direction parallel to the center axis of the elastic webbing 114. The elasticity of the elastic webbing 114 creates a force that opposes the displacement created by the applied force. The elasticity of the elastic webbing 114 returns the elastic webbing 114 to return to its relaxed shape.

The following definitions were used in this disclosure:

Anchor: As used in this disclosure, anchor means to hold an object firmly or securely.

Anchor Point: As used in this disclosure, an anchor point is a location to which a first object can be securely attached to a second object.

Aperture: As used in this disclosure, an aperture is a prism-shaped negative space that is formed completely through a structure or the surface of a hollow structure.

Clip: As used in this disclosure, a clip is a fastener that attaches to an object by gripping or clasping the object. A clip is typically spring loaded.

Composite Textile: As used in this disclosure, a composite textile is a multilayer fabric made of two or more joined layers of textile or sheeting materials.

Disk: As used in this disclosure, a disk is a prism-shaped object that is flat in appearance. The disk is formed from two congruent ends that are attached by a lateral face. The sum of the surface areas of two congruent ends of the prism-shaped object that forms the disk is greater than the surface area of the lateral face of the prism-shaped object that forms the disk. In this disclosure, the congruent ends of the prism-shaped structure that forms the disk are referred to as the faces of the disk.

Elastic: As used in this disclosure, an elastic is a material or object that deforms when a force is applied to it and that is able to return to its relaxed shape after the force is removed. A material that exhibits these qualities is also referred to as an elastomeric material. A material that does not exhibit these qualities is referred to as inelastic or an inelastic material.

Elastic Webbing: As used in this disclosure, an elastic webbing is a webbing that contains elastic yarns as some of the yarns that make up the webbing. An elastic webbing is constructed such that the elastic webbing will stretch when a force is applied and will return to its original shape when after the force is removed.

Fastener: As used in this disclosure, a fastener is a device that is used to join or affix two objects. Fasteners generally comprise a first element which is attached to the first object and a second element which is attached to the second object such that the first element and the second element join to removably attach the first object and the second object. Common fasteners include, but are not limited to, clips, hooks, zippers, magnets, snaps, buttons, buckles, quick release buckles, or hook and loop fasteners.

Filament: As used in this disclosure, a filament is a thread like fiber or object that is used in the production of a yarn.

Grommet: As used in this disclosure, a grommet is an eyelet placed in a hole in a textile, sheet, or panel that protects a rope hook or cable passed through it and to protect the textile, sheet, or panel from being torn.

Major and Minor Axes: As used in this disclosure, the major and minor axes refer to a pair of perpendicular axes that are defined within a structure. The length of the major axis is always greater than or equal to the length of the minor axis. The major axis is always the longest diameter of the structure. The major and minor axes intersect at the center of the structure. The major axis is always parallel to the longest edge of a rectangular structure.

Patient: As used in this disclosure, a patient is a person who is designated to receive a medical treatment, therapy or service. The term patient may be extended to an animal when used within the context of the animal receiving veterinary treatment or services.

Primary Shape: As used in this disclosure, the primary shape refers to a description of the overall geometric shape of an object that is assembled from multiple components.

Prism: As used in this disclosure, a prism is a three-dimensional geometric structure wherein: 1) the form factor of two faces of the prism are congruent; and, 2) the two congruent faces are parallel to each other. The two congruent faces are also commonly referred to as the ends of the prism. The surfaces that connect the two congruent faces are called the lateral faces. In this disclosure, when further description is required a prism will be named for the geometric or descriptive name of the form factor of the two congruent faces. If the form factor of the two corresponding faces has no clearly established or well-known geometric or descriptive name, the term irregular prism will be used. The center axis of a prism is defined as a line that joins the center point of the first congruent face of the prism to the center point of the second corresponding congruent face of the prism. The center axis of a prism is otherwise analogous to the center axis of a cylinder. A prism wherein the ends are circles is commonly referred to as a cylinder.

Relaxed: As used in this disclosure, the term relaxed describes: a) an object that is not subjected to external forces; or, b) a patient that is not subjected to or preoccupied with anxiety. The noun form of relaxed is relaxation.

Relaxed Shape: As used in this disclosure, a structure is considered to be in its relaxed state when no shear, strain, or torsional forces are being applied to the structure.

Rouleau: As used in this disclosure, a rouleau is a tube or channel that is formed on the edge of a textile or sheeting.

Satin: As used in this disclosure, a satin is a smooth fabric made of silk or man-made fibers using a satin weave.

Satin Weave: As used in this disclosure, a satin weave is a weaving pattern in which the face of the fabric is formed almost completely of warp end or weft floats that are produced in the repeat of the weave. The weave produced a characteristic smooth surface on at least one face of the fabric. The satin weave is considered one of the basic weaving patterns. As used in this disclosure satin weaves may be combined with other weave patterns to improve the satin performance characteristics, such as elongation or abrasion resistance, so long as the characteristic smooth surface is maintained.

Seam: As used in this disclosure, a seam is a joining of: 1) a first textile to a second textile; 2) a first sheeting to a second sheeting; or, 3) a first textile to a first sheeting. Potential methods to form seams include, but are not limited to, a sewn seam, a heat bonded seam, an ultrasonically bonded seam, a laser seam, or a seam formed using an adhesive.

Sewn Seam: As used in this disclosure, a sewn seam a method of attaching two or more layers of textile, leather, or other material through the use of a thread, a yarn, or a cord that is repeatedly inserted and looped through the two or more layers of textile, leather, or other material.

Sheeting: As used in this disclosure, a sheeting is a material, such as a paper, textile, a plastic, or a metal foil, in the form of a thin flexible layer or layers. The sheeting forms a disk structure. The two surfaces of the sheeting with the greatest surface area are called the faces of the sheeting.

Silk: As used in this disclosure, the term silk refers to: a) a protein based filament formed by the larvae of insects including a caterpillar known as a silkworm; or, b) a yarn formed from one or more protein based filaments described in the (a) definition.

Textile: As used in this disclosure, a textile is a material that is woven, knitted, braided or felted. Synonyms in common usage for this definition include fabric and cloth. The two surfaces of the textile with the greatest surface area are called the faces of the textile.

Webbing: As used in this disclosure, a webbing is strong, close woven or knitted fabric that is used for straps or belting. As used in this disclosure, webbing is a fully formed material that is only cut to length for use. Webbing is not formed by cutting broader materials into strips. Webbings have tensile strength but are too flexible to provide compressive strength and are not suitable for use in pushing objects. The shape of a webbing is approximated by a rectangular disk shape. The two surfaces of a webbing with the greatest surface area are called the faces of the webbing.

Yarn: As used in this disclosure, a yarn is a continuous strand of textile fibers and filaments. Yarns are generally used in the production of fabrics. For the purposes of this disclosure, this definition explicitly includes yarns formed from a single filament such as a monofilament yarn.

With respect to the above description, it is to be realized that the optimum dimensional relationship for the various components of the invention described above and in FIGS. 1 through 3 include variations in size, materials, shape, form, function, and manner of operation, assembly and use, are deemed readily apparent and obvious to one skilled in the art, and all equivalent relationships to those illustrated in the drawings and described in the specification are intended to be encompassed by the invention.

It shall be noted that those skilled in the art will readily recognize numerous adaptations and modifications which can be made to the various embodiments of the present invention which will result in an improved invention, yet all of which will fall within the spirit and scope of the present invention as defined in the following claims. Accordingly, the invention is to be limited only by the scope of the following claims and their equivalents.

What is claimed is:

1. A pressure-relieving finger-manipulated strip for inducing relaxation in a patient comprising
    a sheeting structure;
    a grommet mounted on the sheeting structure;
    a perimeter rouleau; and
    an elastic webbing attached to a face of the sheeting structure while the elastic webbing is placed under tension such that the elastic webbing draws the sheeting structure in on itself as the elastic webbing returns to its relaxed shape;
    wherein the pressure-relieving finger-manipulated strip is rubbed by the patient to induce relaxation.

2. The pressure-relieving finger-manipulated strip according to claim 1
    wherein the grommet forms an anchor point that allows the pressure-relieving finger-manipulated strip to be clipped to an externally provided structure.

3. The pressure-relieving finger-manipulated strip according to claim 1
    wherein the sheeting structure is flexible; and
    wherein the patient induces relaxation by manipulating the sheeting structure with a hand.

4. The pressure-relieving finger-manipulated strip according to claim 1
    wherein the sheeting structure comprises a textile base and a grommet aperture formed in the textile base.

5. The pressure-relieving finger-manipulated strip according to claim 4
    wherein the grommet attaches to the sheeting structure such that the grommet forms a protective structure around a perimeter of the grommet aperture of the textile base.

6. The pressure-relieving finger-manipulated strip according to claim 4
    wherein the textile base is formed from a plurality of yarns; and
    wherein the textile base is formed using a satin weave pattern.

7. The pressure-relieving finger-manipulated strip according to claim 6
    wherein each of the plurality of yarns used to form the textile base comprises a silk yarn.

8. The pressure-relieving finger-manipulated strip according to claim 4
    wherein the grommet aperture is an aperture that is formed by faces of the textile base; and wherein a perimeter of the grommet aperture is protected by the grommet.

9. The pressure-relieving finger-manipulated strip according to claim 1
wherein the perimeter rouleau forms a structure on the face of the sheeting structure that encloses the elastic webbing.

10. The pressure-relieving finger-manipulated strip according to claim 9
wherein the perimeter rouleau further comprises one or more seams; and
wherein the one or more seams are used to form the perimeter rouleau by securing a perimeter of the sheeting structure to the face of the sheeting structure.

11. The pressure-relieving finger-manipulated strip according to claim 10
wherein each of the one or more seams is a sewn seam.

12. The pressure-relieving finger-manipulated strip according to claim 1
wherein the elastic webbing is an elastic textile-based structure;
wherein the elastic webbing attaches to the face of the sheeting material such that the elastic webbing is enclosed by the perimeter rouleau.

* * * * *